US00PP12642P2

(12) United States Plant Patent
Pouw

(10) Patent No.: US PP12,642 P2
(45) Date of Patent: May 21, 2002

(54) MINIATURE ROSE PLANT NAMED 'RUIABRI'

(75) Inventor: Antonius A. Pouw, De Kwakel (NL)

(73) Assignee: DeRuiter Nieuwe Rozen B.V., De Kwakel (NL)

( * ) Notice: Subject to any disclaimer, the term of this patent is extended or adjusted under 35 U.S.C. 154(b) by 0 days.

(21) Appl. No.: 09/480,598

(22) Filed: Jan. 10, 2000

(51) Int. Cl.[7] ..... A01H 5/00
(52) U.S. Cl. ..... Plt./120
(58) Field of Search ..... Plt./120, 116, 119, Plt./121

(56) References Cited

PUBLICATIONS

UPOV–ROM GTITM Computer Database 2001/01, Feb. 6, 2001, GTI Jouve Retrieval Software, Citation for 'Ruiabri'.*

* cited by examiner

*Primary Examiner*—Bruce R. Campell
*Assistant Examiner*—June Hwu
(74) *Attorney, Agent, or Firm*—C. A. Whealy

(57) ABSTRACT

A distinctive cultivar of miniature rose plant named 'Ruiabri', characterized by its dark green leaves; large double salmon-colored flowers; flowers arranged singly or in large sprays; strong rooting habit; excellent postproduction longevity; and excellent garden performance.

2 Drawing Sheets

BACKGROUND OF THE INVENTION

The present invention relates to a new and distinct cultivar of the miniature rose class, botanically known as *Rosa hybrida*, and hereinafter referred to by the cultivar name Ruiabri.

The new cultivar is a product of a planned breeding program conducted by the Inventor in Hazerswoude, The Netherlands. The objective of the breeding program was to develop compact pot rose varieties with novel and attractive flower colors and excellent postproduction longevity and garden performance. The new cultivar originated from a cross made by the Inventor in 1994 of two unnamed proprietary seedlings, not patented. The cultivar Ruiabri was discovered and selected by the Inventor as a flowering plant within the progeny of the stated cross in a controlled environment in Hazerswoude, The Netherlands. Plants of the new cultivar differ from plants of the parent selections primarily in flower color.

Asexual reproduction of the new cultivar by cuttings taken at Hazerswoude, The Netherlands, has shown that the unique features of this new miniature rose plant are stable and reproduced true to type in successive generations of asexual reproduction.

SUMMARY OF THE INVENTION

The following traits have been repeatedly observed and are determined to be the unique characteristics of 'Ruiabri'. These characteristics in combination distinguish the new miniature rose plant as a new and distinct cultivar:

1. Dark green leaves.
2. Large double salmon-colored flowers.
3. Flowers arranged singly or in large sprays.
4. Strong rooting habit.
5. Excellent postproduction longevity.
6. Excellent garden performance.

The new miniature rose plant has not been observed under all possible environmental conditions. The phenotype may vary significantly with variations in environment such as temperature and light level, without, however, any variance in genotype.

BRIEF DESCRIPTION OF PHOTOGRAPHS

The accompanying colored photographs illustrate typical specimens of the vegetative growth and flowers of the new miniature rose plant, showing the colors as true as it is reasonably possible to obtain in colored reproductions of this type. Colors in the photographs may differ slightly from the color values cited in the detailed botanical description which more accurately describe the actual colors of the new miniature rose.

The photograph at the top of the first sheet comprises a top perspective view of a typical plant of the new miniature rose plant grown in Hazerswoude, The Netherlands.

The photograph at bottom of the first page comprises a close-up view of a typical flower of the new miniature rose plant.

The photograph on the second sheet comprises details of the new miniature rose plant. In this photograph the apex of a young shoot (1); a leaf with three leaflets (2); a leaf with five leaflets (3); a leaf with seven leaflets (4); a stem without leaves (5); a flower bud after sepals open (6); a flower bud after petals begin to unfurl (7); a flower one-half open (8); a flower fully open (9); reproductive organs (10); a pistil (11); and receptacle (12) are shown.

DETAILED BOTANICAL DESCRIPTION

The following observations and measurements describe plants grown in Keller, Tex., in 15-cm containers under conditions which closely approximate commercial outdoor production conditions during the summer and early autumn. Plants used for the description were about 15 weeks old.

In the following description, color references are made to The Royal Horticultural Society Colour Chart except where general terms of ordinary dictionary significance are used.

Classification:

*Botanical.*—*Rosa hybrida* cultivar Ruiabri.

*Commercial.*—Miniature pot rose.

Parentage:

*Male or pollen parent.*—Unnamed proprietary seedling, not patented.

*Female or seed parent.*—Unnamed proprietary seedling, not patented.

Propagation:

*Type.*—Terminal or stem cuttings.

*Time to rooting.*—8 to 10 days with soil temperatures of 20° C.

*Root description.*—Propagates easily, roots and well-branched.

Plant description:

*Form.*—Upright, somewhat spreading; uniform habit.

*Plant height.*—About 36 cm.

*Plant width.*—About 38 cm.

*Growth habit.*—Vigorous. Suitable for 10-cm and larger containers.

*Crop time.*—Time to produce a finished plant in a 10-cm container 20 to 30 cm in height and 15 to 20 cm in width is generally about 10 to 12 weeks depending on average temperature, light level, and cultural practices.

*Stem and lateral branches.*—Branching habit: Freely; branches will potentially form at every node. Diameter of lateral branches, at base: About 4 mm. Internode length: About 1.4 cm. Texture: Smooth. Color: 137A. Thorns: Amount: Moderate. Length: About 4 mm. Shape: Linear. Color: Light brown, close to 164C when immature, darker brown, close to 177A when mature.

*Foliage description.*—Leaves arranged alternately, compound with typically three to seven leaflets per leaf, generally symmetrical, abundant, and flat in aspect. Stipules at petiole base; stipules about 7 mm in length, linear and pointed, glabrous, and similar in color to leaf. Leaflet length: about 2.5 cm. Leaflet width: About 1.7 cm. Shape: Ovate. Apex: Acute. Base: Obtuse. Margin: Serrate. Texture: Upper surface, glossy; lower surface, dull. Petiole length: About 1.6 cm to base of lower leaflet. Rachis length: About 2 cm. Petiole diameter: About 1 mm. Color: Young foliage, upper surface: Darker than 144A, overlain with anthocyanin, close to 59A. Young foliage, lower surface: Close to 147B, overlain with anthocyanin, close to 59A. Mature foliage, upper surface: 147A. Mature foliage, lower surface: 147B. Petiole: Upper surface, 147A overlain with close to 59A; lower surface, 147B.

Flower description:

*Flower type and habit.*—Large double salmon flowers. Consistently symmetrical rosette flowers that are hemispherical in shape. Freely and continuously flowering. The flowers are borne singly on peduncles or arranged in large sprays with about three flowers per spray. Flowers persistent.

*Flowering season.*—Year-round under greenhouse conditions, optimal flowering from spring through autumn under garden conditions.

*Flower diameter.*—About 4.2 cm.

*Flower depth* (*height*).—About 2.1 cm.

*Flower longevity on plant.*—About 12 to 14 days.

*Fragrance.*–Very faint, typical of Rosa.

*Fower buds* (*at stage of showing color*).—Shape: Ovoid. Length: About 1.3 cm. Diameter: About 1 cm. Color: Close to 47C.

*Petals.*—Quantity: About 78 per flower; typically about 13 rows, rosette arrangement. Length, outer petals: About 2.1 cm. Width, outer petals: About 2.2 cm. Shape: Roughly cordate. Apex: Retuse or cuspidate. Base: Attenuate. Margin: Entire, recurved. Texture: Smooth, velvety. Color: When opening, upper surface: 47C; base, white, close to 155D. When opening, lower surface: 47D; base, white, close to 155D. Fully opened, upper surface: 47C to 47B; fading to 47D with subsequent development; base; white, close to 155D. Fully opened, lower surface: 47D to 47C; base, white, close to 155D.

*Sepals.*—Quantity: Typically five per flower. Length: About 2.1 cm. Diameter: About 6 mm. Shape: Narrowly ovate. Apex: Sharply pointed. Base: Truncate. Texture: Pubescent, fine white hairs on upper surface. Color: Upper surface; 144A; covered with fine white hairs. Lower surface: 144A.

*Peduncles.*—Strength: Good yet flexible. Aspect: Erect to bent. Length: About 3.1 cm. Texture: Glabrous. Color: Close to 137A, occasionally overlain with anthocyanin, close to 59A.

*Reproductive organs.*—Stamens: Quantity: About 25 per flower. Anther size: About 2 by 1.5 mm. Anther shape: Bilobate. Anther color: Close to 7A. Pistils: Quantity: About 20 per flower. Style length: About 4.5 mm. Style color: Close to 4D.

*Seed.*—Seed production has not been observed.

Disease/pest resistance: Plants of the new miniature rose have been shown to be resistant to Powdery Mildew. Resistance to pest has not been observed.

Temperature tolerance: Plants of the new miniature rose have been shown to be tolerant to temperatures from 0 to 45° C.

It is claimed:

1. A new and distinct miniature rose plant named 'Ruiabri', as illustrated and described.

* * * * *

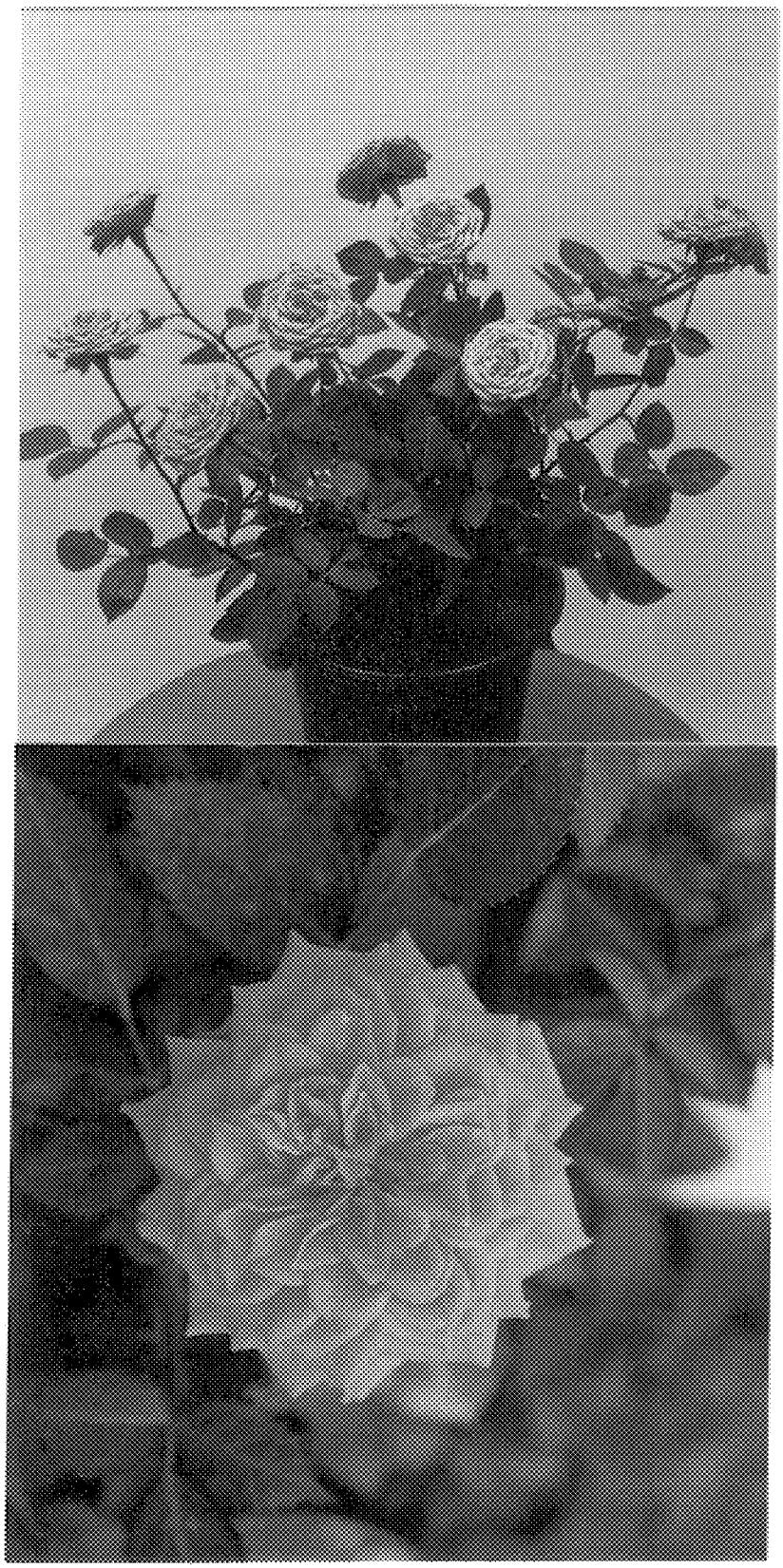

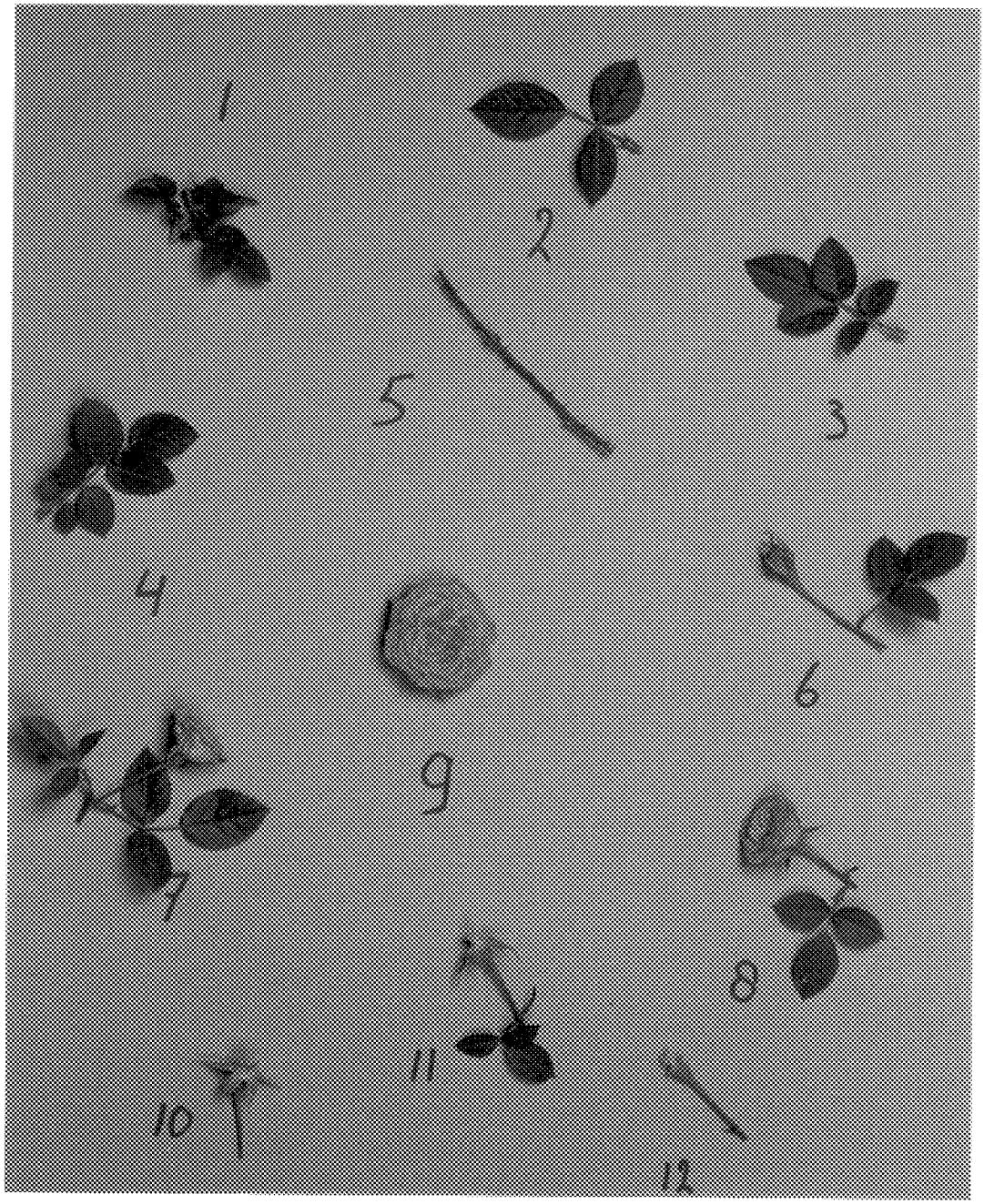
1
2
3
4
5
6
7
8
9
10
11
12